United States Patent [19]

Vidal

[11] 4,254,771
[45] Mar. 10, 1981

[54] FOLDED TOP URINE BAG WITH ELONGATED STIFFENING PANEL

[75] Inventor: Claude A. Vidal, Los Angeles, Calif.

[73] Assignee: American Hospital Supply Corporation, Evanston, Ill.

[21] Appl. No.: 936,822

[22] Filed: Aug. 25, 1978

[51] Int. Cl.³ .............................................. A61F 5/44
[52] U.S. Cl. .......................... 128/275; 128/DIG. 24; 229/54 R; 229/55
[58] Field of Search .............. 128/272, 275, 276, 283, 128/DIG. 24, 278, 295, 227, 224, 214 D, 767; 150/0.5, 1, 8, 12; 190/58 R, 57; 229/52, 55, 52 A, 54 R

[56] References Cited

U.S. PATENT DOCUMENTS

| | | | |
|---|---|---|---|
| 2,811,968 | 11/1957 | Hyatt | 128/DIG. 24 |
| 2,878,849 | 3/1959 | Lingenfelter et al. | 150/0.5 |
| 3,090,968 | 5/1963 | Buono | 4/110 |
| 3,253,593 | 5/1966 | Cronin, Jr. | 128/275 |
| 3,312,221 | 4/1967 | Overment | 128/DIG. 24 |
| 3,366,312 | 1/1968 | Lowenberg et al. | 229/55 |
| 3,415,299 | 12/1968 | Hinman, Jr. et al. | 150/8 |
| 3,509,879 | 5/1970 | Bathish et al. | 128/214 |
| 3,537,456 | 11/1970 | Harautuneian | 128/275 |
| 3,568,965 | 3/1971 | Clark | 248/95 |
| 3,661,153 | 5/1972 | Polk et al. | 128/275 |
| 3,699,964 | 10/1972 | Ericson | 128/275 |
| 3,802,418 | 4/1974 | Clayton | 128/283 |
| 3,998,255 | 12/1976 | Mather et al. | 128/275 |
| 4,085,755 | 4/1978 | Burrage | 128/275 |
| 4,119,268 | 10/1978 | Segura | 229/54 R |

FOREIGN PATENT DOCUMENTS

| | | | |
|---|---|---|---|
| 475595 | 7/1951 | Canada | 190/58 R |
| 1129010 | 1/1957 | France | 128/DIG. 24 |

OTHER PUBLICATIONS

Webster's Seventh New Collegiate Dictionary, G & C Merriam Co., Springfield, Mass. 1963, p. 439 "Integral".

Primary Examiner—Robert W. Michell
Assistant Examiner—J. L. Kruter
Attorney, Agent, or Firm—Larry N. Barger

[57] ABSTRACT

A urine collection bag with a folded over top sealed to a stiffening panel in a generally horizontal plane. This panel shapes the folded bag top to define a ventable gas pocket immediately below the panel. The panel has a handle flexibly connected to it for suspending the bag with its gas pocket upright. The bag construction also discloses an inverted J-shaped opaque wall structure sealed to a transparent wall.

23 Claims, 9 Drawing Figures

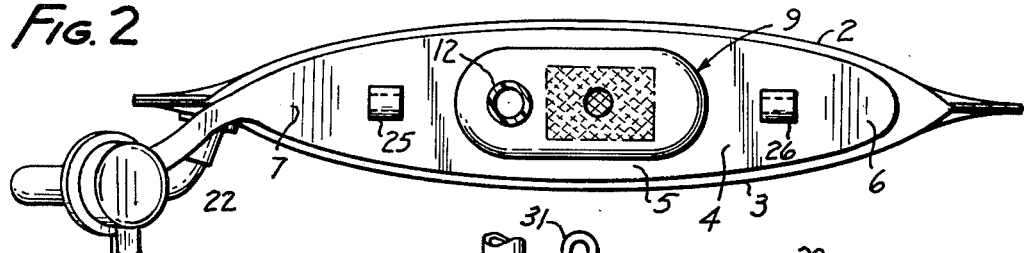
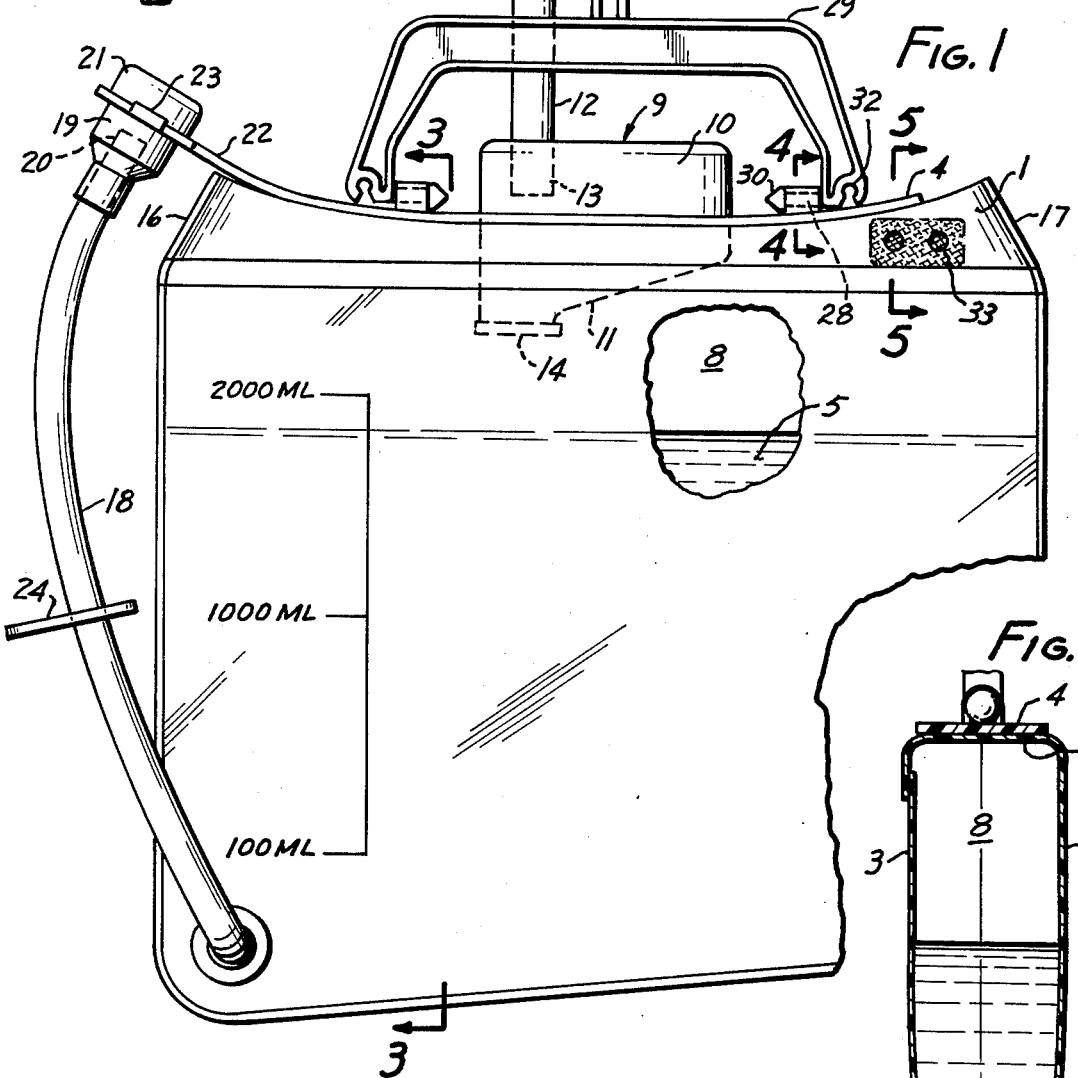
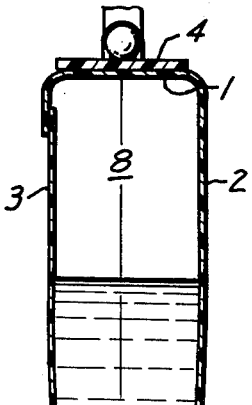
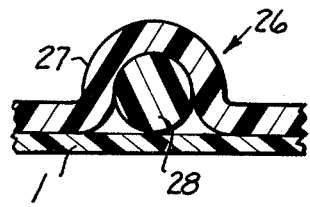
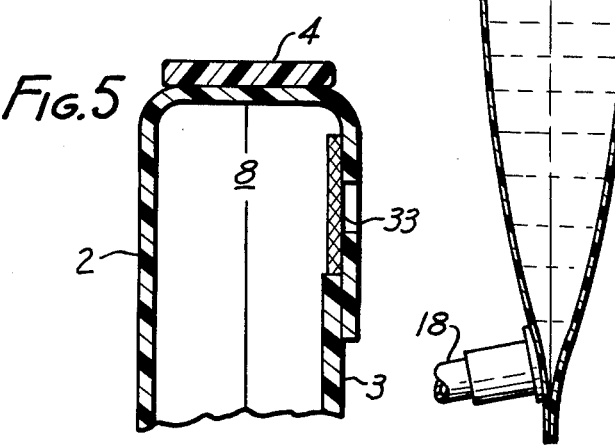

FOLDED TOP URINE BAG WITH ELONGATED STIFFENING PANEL

BACKGROUND

Urinary drainage bags are frequently used in hospitals to collect urine from patients over considerable lengths of time. Typically, a urethral catheter is inserted in the patient and the catheter connected to a urinary drain tube which leads to a collection bag attached to the bed rail or the like. These bags are periodically emptied, and every effort is made to prevent any bacterial contamination that might grow in the collected urine from migrating back to the patient's bladder, causing a urethral or bladder infection.

In recent years, it has been the practice to include drip housings, valves, and other air breaks in the line between the patient and the collection bag. Because the urine collection bags are disposed of after a single patient use, they must be made very inexpensively and very reliable relative to leakage.

One type of urine bag construction has included two flap flexible panels sealed together about their peripheries with tubular inlet and outlet ports sealed between the two superimposed panels (U.S. Pat. No. 3,415,299) or sealed to a side wall of the bag (U.S. Pat. No. 3,568,965). The former patent has a practical drawback in that it is difficult to reliably seal two flat sheets around a tubular neck. Sealing inlet and outlet ports to a bag side wall often requires expensive elbow connections and such connections to a highly flexible bag wall are difficult to control as the bag is moved about.

In a different field of blood collection and dispensing bags, it has been proposed to use a "folded" top structure with a stiffening saddle carrying the port structure to the bag's top (U.S. Pat. No. 3,509,879). Here the blood bag was supported on a wire hook of a separate I.V. stand which hooked into a flexible extension of the bag wall itself. There was no hanger structure mounted on the rigidifying saddle which was the firmest and most easily controllable part of the blood bag. Handling a filled blood bag is somewhat similar to handling a water-filled balloon. However, this did not pose a significant problem in blood bags which are of approximately one pint capacity. Handling a sloppy urine collection bag of 2,000 ml capacity (approximately ½ gal.) or more is more difficult without a firm handle control. Skewer type wire hangers (U.S. Pat. No. 3,090,968) lack the firm control and support for the bag.

It is desirable to vent the flexible bag (U.S. Pat. No. 3,568,965) with a hydrophobic vent. However, when the vent is in imminent contact with an opposing wall of the bag, sometimes urine can collect for long periods of time at the vent area with the two walls having a somewhat capillary action in holding the urine. This might happen if the bag were temporarily tilted to barely wet the filter. A wet filter over long periods of time could become clogged with urinary salts which could substantially reduce its venting and filtering efficiency. This is much less likely to happen where the bag wall filter is based a substantial distance from its opposing wall. Also, bag walls that are held in separated condition in an area of the liquid inlet help reduce the chance of retrograde bacterial growth even though with tilting and flexing of the bag during use a limited area of the bag's inlet structure could come in contact with one or both of the bag's side walls.

SUMMARY OF THE INVENTION

The present invention overcomes the problems mentioned above by providing a urine collection bag with a folded over top which eliminates the hard to control process of sealing a round tube sandwiched between two separate walls of a bag. This invention has a stiffening panel lying in an approximately horizontal plane sealed at a flat surface to surface bond with the top. The stiffening panel has substantial width and shapes the top to provide an inner pocket immediately below the panel to help space a substantial portion of the bag wall from circumferentially clinging to an inlet structure of the liquid inlet and reduce the chance of retrograde bacterial growth. Preferably, the bag has a hydrophobic vent into the gas pocket (such as an air pocket) which is positioned to be out of contact with opposing wall structure of the bag. A handle is flexibly joined to the stiffening panel. The bag's top and one side wall are preferably of an integral opaque film material while the opposite side wall is of a transparent film material.

THE DRAWINGS

FIG. 1 is a front elevational view of the urine collection bag with attached handle;

FIG. 2 is a top elevational view of the urine collection bag with handle detached;

FIG. 3 is a sectional view taken along line 3-3 of FIG. 1 with handle removed;

FIG. 4 is an enlarged sectional view taken along line 4-4 of FIG. 1; and

FIG. 5 is an enlarged sectional view taken along line 5-5 of FIG. 1.

DETAILED DESCRIPTION

FIG. 1 shows a urine collection bag with a folded over top wall 1 joined to depending side walls 2 and 3. (See FIG. 3). Top 1 has a short depending section which is bonded to wall 3. Thus, the combined walls 1 and 2 have an inverted J-shape with a depending lip secured to a side wall of the bag forming a seam. Preferably, walls 1 and 2 are opaque to provide a background to transparent wall 3. Sealed to top wall 1 by conductive, R.F. or ultrasonic sealing means is a stiffening panel 4 which lies in a generally horizontal plane, although it is slightly curved upwardly at its end portions due to its shaping of the bag's top 1. Preferably, stiffening panel 4 and the bag are of thermplastic material with the stiffening panel 4 being substantially thicker.

The stiffening panel has a substantially wider center portion 5 and narrowing ends 6 and 7 giving the stiffening panel a generally oval shape. Were it not for stiffening panel 4, the folded over top 1 would resemble a straight line fold as shown in U.S. Pat. No. 3,090,968. However, with the widened central area of stiffening panel 4, the depending side walls 2 and 3 take on a somewhat spaced oval configuration at their upper areas which defines an air pocket 8 immediately below panel 4. Air pocket 8 is widest immediately adjacent a drip housing 9 supported on the stiffening panel 4. Preferably, the drip housing 9 has an upper portion 10 integrally formed with the panel 4 and a lower portion 11 sealed to an inner surface of the bag's top which is in turn sealed to stiffening panel 4. An opening (not shown) for the bag's top inside drip housing provides communication between upper and lower sections 10 and 11 of the drip housing. Thus, urine draining through tube 12 with extending drip tube 13 can exit through an outlet check valve 14 of the drip chamber.

The stiffening panel 4 that spaces apart the depending side walls 2 and 3 substantially reduce the area of possible contact between the side walls and the outlet valve 14. However, it is understood that certain positions of the bag and limited areas of the drip housing adjacent check valve 14 can contact certain small areas of the bag's side wall. However, this is in the air pocket 8 above the urine 15 substantially reducing the chance of retrograde contamination from the bag's collected urine.

Because of the shaping of the generally straight line fold of the bag's top 1 into a spaced oval shape as shown in FIG. 2, the stiffening panel 4 has a slight downward curve at its middle (FIG. 1) giving the bag's upper portion a somewhat "pagoda" shape. Preferably, the outer wings of the pagoda shape are minimized by inwardly slanting seals 16 and 17 at upper ends of vertical side seals on the bag. These slanting seals 16 and 17 reduce the chance of urine accumulating in the dark bag corners and being held there by surface tension even after the bag is emptied. The bag structure shown in FIG. 1 permits very smooth and clean emptying of the bag through a bottom drain tube 18 that includes an enlarged protector housing 19 surrounding a dispensing tip 20 of drain tube 18. During collection of the urine from a patient, enlarged protector housing 19 is closed by a cap 21 which is integrally formed with stiffening panel 4 and flexibly secured to panel 4 by a narrow web 22. When the bag is emptied, cap 21 is removed from housing 19 with the aid of a pull tab 23, and urine is drained from the bag. A clamp 24 is schematically shown as a slide clamp for opening and closing tube 18. However, it is understood that other types of clamps, such as pinch clamps, could also be used.

The stiffening panel 4 includes a pair of axially aligned upstanding bearing journals 25 and 26. FIG. 4 shows these bearing journals formed of an upstanding inverted U-shaped portion 27 sealed to the bag top 1 making a circumferentially enclosed bearing journal that is open on both ends. The term "bearing journal" is used in its broadest sense to include a housing or tube in which a shaft 28 of handle 29 can rotate. Preferably, the inverted U-shaped portion is of a temporarily distortable thermoplastic material into which shaft 28 of panel 29 can snap and be held in place by an integral conically shaped head structure 30 on shaft 28. As shown in FIG. 1, both the bearing journals and opposed shaft of handle 29 are coaxial.

For supporting the urine collection from a bed rail, a U-shaped member 31 can be provided on handle 29 for connecting with a hook structure. The handle can include cord hanger structure at 32, which is the subjet of a co-owned co-pending application, Ser. No. 936,758, filed Aug. 25, 1978, now U.S. Pat. No. 4,189,789 invented by Jack H. Hofstetter, and entitled, "Urine Collection Container with Coupling For Suspension Line."

In FIG. 5, the stiffening panel 4 shapes the top so as to provide air pocket 8 adjacent hydrophobic filter 33 so that wall 2 is not likely to trap urine against filter 33 for a long time wetting effect which might reduce the filter's efficiency through deposits of evaporated salts on the filter from the urine. The hydrophobic filter 33 works well when located adjacent one of the upwardly curved end portions of the stiffening panel. The process and structure of physically sealing hydrophobic vent 33 to a flexible wall with improved adhesion is described in a co-owned co-pending application, Ser. No. 936,754, entitled, "Medical Liquid Container With Filter Vent," by Jack H. Hofstetter, and filed Aug. 25, 1978, which application was abandoned concurrently with filing a streamlined continuation application mailed to the Patent Office on Apr. 16, 1980.

In the above description, a specific example has been used to describe the invention. However, it is understood by those skilled in the art that certain modifications can be made to this example without departing from the spirit and scope of the invention.

I claim:

1. A urine collection bag with a liquid inlet and a folded over top adjoined to depending side walls, wherein the improvement comprises: a stiffening panel being generally horizontal in both its length and width directions with upwardly curving end portions and having a length substantially greater than its width, which panel is sealed to the bag along its top to horizontally spread apart a top portion of the bag to define a gas pocket immediately below the panel; a hydrophobic vent connected to the bag adjacent at least one of the upwardly curving end portions of the stiffening panel for venting the gas pocket; which panel has a pair of spaced apart anchor means for a hanger, and a flexible hanger connected to the pair of anchor means of the panel for suspending the bag with its gas pocket upright.

2. A urine collection bag as set forth in Claim 1, wherein the bag has opposed side walls and these side walls have edge seams with upper portions that slant inwardly toward ends of the panel.

3. A urine collection bag as set forth in claim 1, wherein there is a drip housing that includes the liquid inlet mounted on the panel.

4. A urine collection bag as set forth in claim 1, wherein the flexible hanger includes a handle pivotally connected to the panel.

5. A urine collection bag as set forth in claim 4, wherein the panel includes at least one bearing journal and the handle has a shaft pivotally received in the bearing journal.

6. A urine collection bag as set forth in claim 5, wherein the panel has two spaced apart axially aligned bearing journals, and the handle has two spaced apart axially aligned shafts pivotally received in these journals.

7. A urine collection bag as set forth in claim 5, wherein the bearing journal is sufficiently distortable for assembly of the handle when such handle has an enlarged retention head on its shaft.

8. A urine collection bag as set forth in claim 1, wherein the bag and stiffening panel are of thermoplastic material.

9. A urine collection bag with a liquid inlet and a folded over top joined to two depending opposed side walls, wherein the improvement comprises: a stiffening panel being generally horizontal in both its length and width directions with upwarding curving end portions and having a length substantially greater than its width sealed to and horizontally spreading apart a top portion of the bag to define a gas pocket immediately below the panel; a hydrophobic vent connected to the bag adjacent at least one of the upwardly curving end portions of the stiffening panel for venting the gas pocket; which panel has a pair of spaced apart anchor means for a hanger; a flexible hanger connected to the pair of anchor means of the panel for suspending the bag with its gas pocket upright; and said bag having one transparent side wall and one opaque side wall.

10. A urine collection bag as set forth in claim 9, wherein the top is opaque and integral with the opaque side wall.

11. A urine collection bag as set forth in claim 9, wherein the bag has a transverse seam adjacent the panel joining the opaque and transparent side walls of the bag.

12. A urine collection bag as set forth in claim 11, wherein the top and one side wall are integral.

13. A urine collection bag as set forth in claim 12, wherein the integral top and side walls are opaque.

14. A urine collection bag with a liquid inlet and a folded over top joined to depending side walls, wherein the improvement comprises: a stiffening panel being generally horizontal in both its length and width directions with upwardly curving end portions and having a length substantially greater than its width sealed to and horizontally spreading a top portion of the bag to define a gas pocket immediately below the panel, which panel is wider at its central area than at its ends; a drip housing mounted on the panel and having a liquid inlet; a hydrophobic vent on the bag adjacent at least one of the upwardly curving end portions of the stiffening panel for venting the gas pocket; which panel has a pair of spaced apart anchor means for receiving a suspension member; and a suspension member connected to the pair of anchor means for suspending the bag with the gas pocket upright.

15. A urine collection bag with a liquid inlet and a folded over top adjoined to depending side walls, wherein the improvement comprises: a stiffening panel sealed to and top portion of the bag to define a gas pocket immediately below the panel, which top extends in an approximately horizontal plane in both its length and width directions with upwardly curving end portions when the bag is suspended vertically, and the panel is wider at its central area than at its ends to horizontally spread apart a top portion of the bag; a hydrophobic vent connected to the bag adjacent at least one of the upwardly curving end portions of the stiffening panel for venting the gas pocket; which panel has a pair of spaced apart anchor means for a hanger; and a flexible hanger connected to the pair of anchor means of the panel for suspending the bag with its gas pocket upright.

16. A urine collection bag as set forth in claim 15, wherein the side walls have edge seams with upper portions that slant inwardly toward ends of the panel.

17. A urine collection bag with a liquid inlet and a folded over top adjoined to depending side walls, wherein the improvement comprises: a stiffening panel being generally horizontal in both its length and width directions with upwardly curving end portions and being sealed to and horizontally spreading a top portion of the bag to define a gas pocket immediately below the panel; a hydrophobic vent connected to the bag adjacent at least one of the upwardly curving end portions of the stiffening panel for venting the gas pocket; an integrally connected closure on the panel; a bottom outlet drain with enlarged tip protector housing that is releasably secured to the closure; which panel has a pair of spaced apart anchor means for a hanger; and a flexible hanger connected to the pair of anchor means of the panel for suspending the bag with its gas pocket upright.

18. A urine collection bag as set forth in claim 17, wherein the closure is a cap joined to the panel by a flexible web.

19. A urine collection bag with a liquid inlet and a folded over top adjoined to depending side walls, wherein the improvement comprises: a stiffening panel sealed to and shapingly forming a top of the bag to define a gas pocket immediately below the panel; at least one inverted U-shaped bearing journal on the panel, which bearing journal has at least one open end with the bag's top spanning a mouth of such journal structure to circumferentially enclose the journal; and a hanger with a shaft pivotally connected in the panel's journal for suspending the bag with its gas pocket upright.

20. A urine collection bag as set forth in claim 19, wherein the bearing journal is sufficiently distortable for assembly of the handle when such handle has an enlarged retention head on its shaft.

21. A vented urine collection bag with a liquid inlet and a folded over top adjoined to depending side walls, wherein the improvement comprises: a stiffening panel having a length substantially greater than its width, which panel is sealed to the bag along its top to shapingly form a top of the bag and space apart its side walls to define a gas pocket immediately below the panel; which panel has at least one bearing journal that includes an inverted generally U-shaped structure with at least one open end and the bag's top spans a mouth of such structure to circumferentially enclose the journal; and a flexible hanger having a shaft pivotally received in the bearing journal connected to the panel for suspending the bag with its gas pocket upright.

22. A vented urine collection bag with a liquid inlet and a folded over top adjoined to depending side walls, wherein the improvement comprises: a stiffening panel having a length substantially greater than its width, which panel is sealed to the bag along its top to shapingly form a top of the bag and space apart its side walls to define a gas pocket immediately below the panel; a flexible hanger connected to the panel for suspending the bag with its gas pocket upright; the bag having two opposed side walls, one opaque and the other sufficiently transparent to view the contents of the bag; and the transparent side wall is sealed to the top along a transverse seam adjacent the panel with the opaque top and opaque side wall being integral and forming a generally inverted J-shape with a depending lip secured to a side wall of the bag forming a seam.

23. A vented urine collection bag with a liquid inlet and a folded over top joined to two depending opposed side walls, wherein the improvement comprises: a stiffening panel having a length substantially greater than its width sealed to and shapingly forming the bag top and space apart its side walls to define a gas pocket immediately below the panel; said bag having one transparent side wall and one opaque side wall; a transverse seam adjacent the panel joining the opaque and transparent side walls of the bag; and the top is opaque and integral with the opaque side walls to form an opaque section of the bag that has a generally inverted J-shape with a depending lip secured to a side wall of the bag forming a seam.

* * * * *